United States Patent [19]
Forster

[11] Patent Number: 6,158,583
[45] Date of Patent: Dec. 12, 2000

[54] HAEMOSTATIC CLIP HOLDER

[75] Inventor: Michel Forster, Beaumont-lès-Valence, France

[73] Assignee: Vitalitec International, France

[21] Appl. No.: 09/230,780

[22] PCT Filed: Jul. 29, 1997

[86] PCT No.: PCT/FR97/01410

§ 371 Date: Jan. 29, 1999

§ 102(e) Date: Jan. 29, 1999

[87] PCT Pub. No.: WO98/05260

PCT Pub. Date: Dec. 2, 1998

[30] Foreign Application Priority Data

Aug. 1, 1996 [FR] France .................................. 96 09921

[51] Int. Cl.[7] .................................................. B65D 85/00
[52] U.S. Cl. .......................................... 206/339; 206/340
[58] Field of Search .................................. 206/338–340; 606/157

[56] References Cited

U.S. PATENT DOCUMENTS

| | | |
|---|---|---|
| 4,076,120 | 2/1978 | Carroll et al. . |
| 4,146,130 | 3/1979 | Samuels et al. ......................... 206/340 |
| 4,294,355 | 10/1981 | Jewusiak et al. . |
| 4,961,499 | 10/1990 | Kulp . |
| 5,908,430 | 6/1999 | Appleby .................................... 206/339 |

FOREIGN PATENT DOCUMENTS

| | | |
|---|---|---|
| 0482861 | 4/1992 | European Pat. Off. . |
| 0583151 | 2/1994 | European Pat. Off. . |
| WO91 04925 | 4/1981 | WIPO . |

*Primary Examiner*—Jim Foster
*Attorney, Agent, or Firm*—Blakely Sokoloff Taylor & Zafman

[57] ABSTRACT

The support (1) which is in the form of an elongate strip, possesses clip supporting and retaining means which co-operate solely with web portions (51–52) of a clip (5) leaving the lateral limbs (50) thereof free; the support means comprise at least one bearing face (200) against which the web portion (51–52) of a clip rests, while the retaining means comprise a thin flexible tongue forming a blocking tab of a length that is not less than the height of the clip, and normally bearing against the web portion (52), but capable of moving away therefrom along a path that is substantially perpendicular to the plane of the clip in order to release it when an upwardly-directed traction force is exerted on the clip. The support is applicable to surgical equipment.

8 Claims, 4 Drawing Sheets

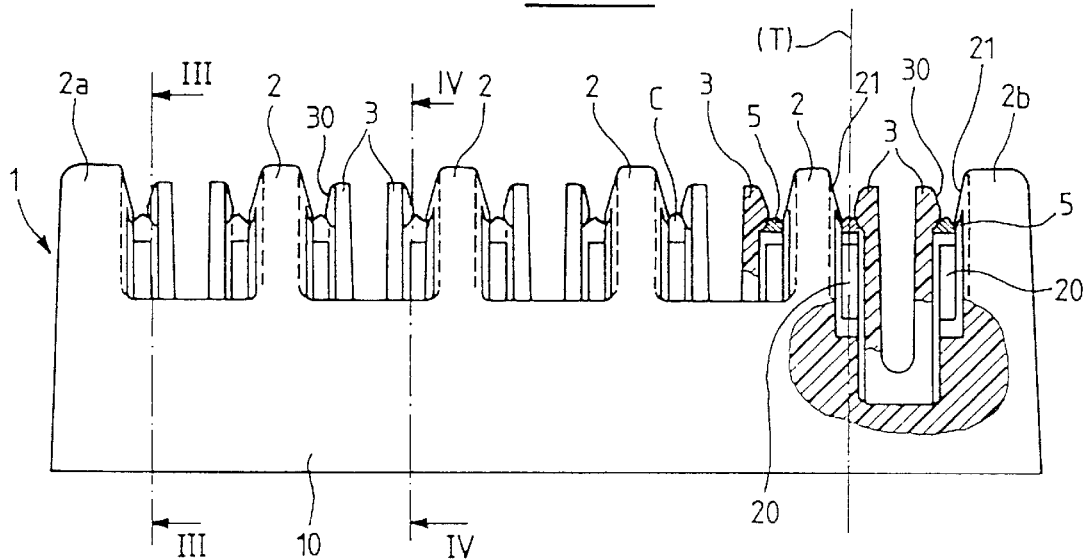
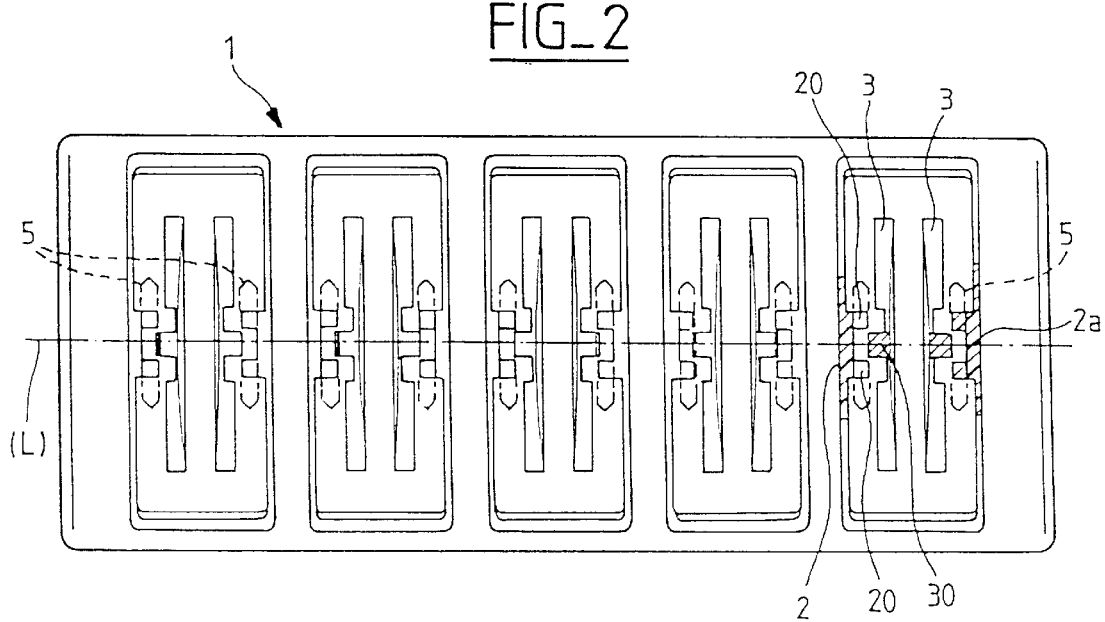

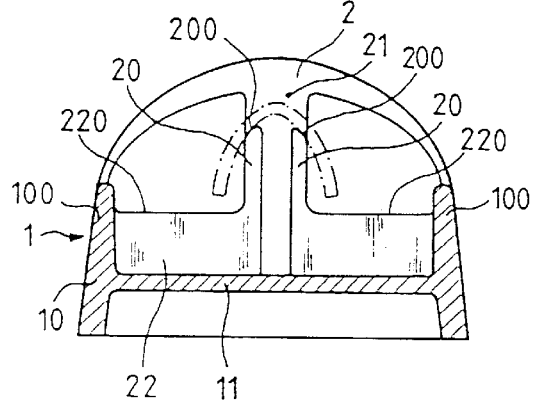
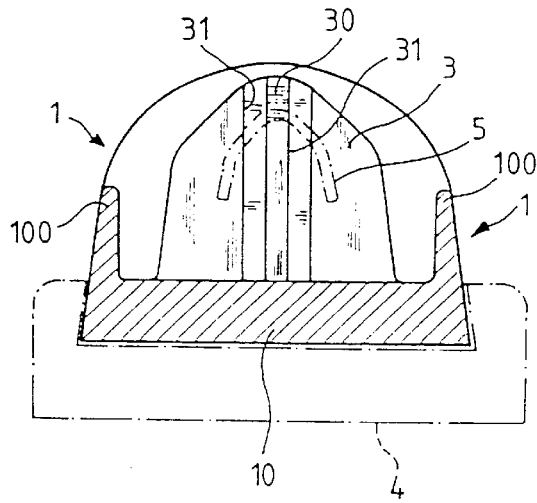
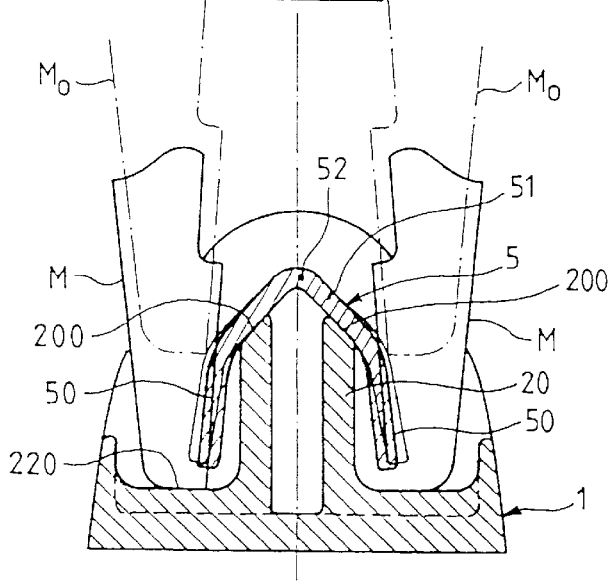
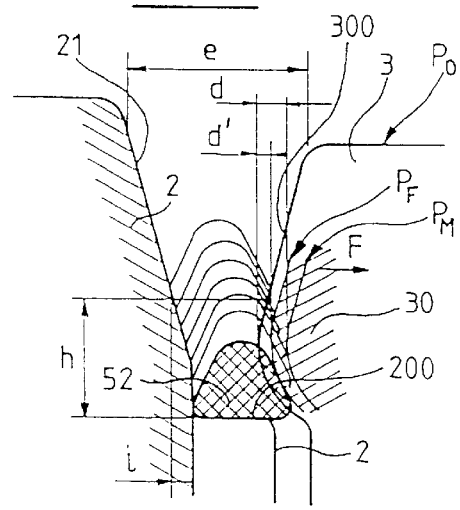

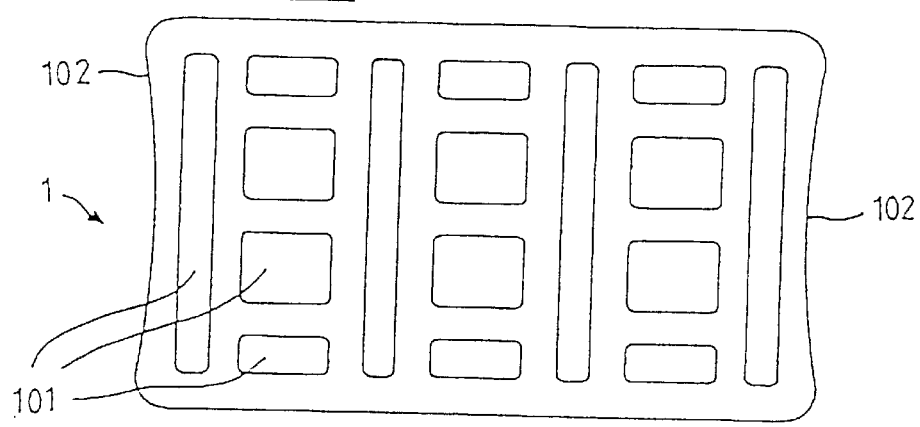
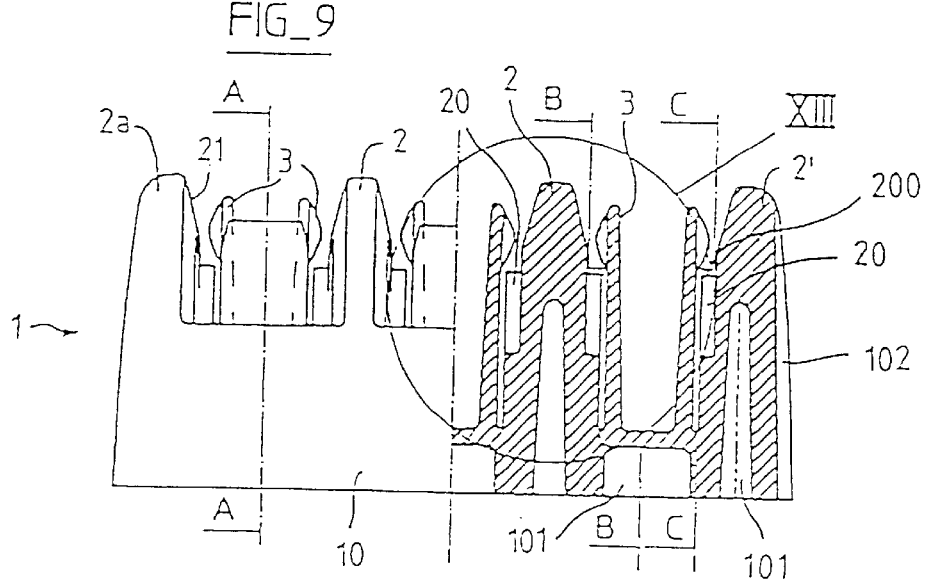
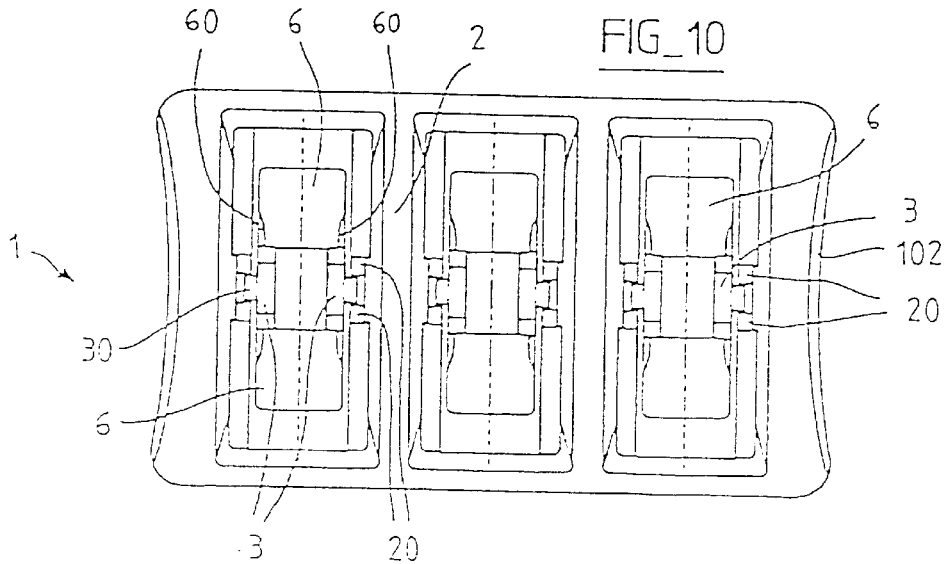

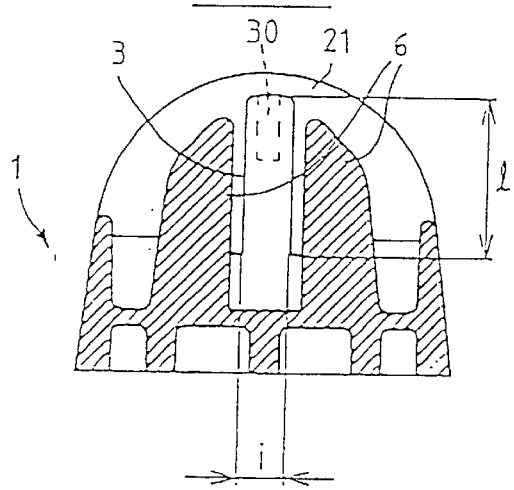
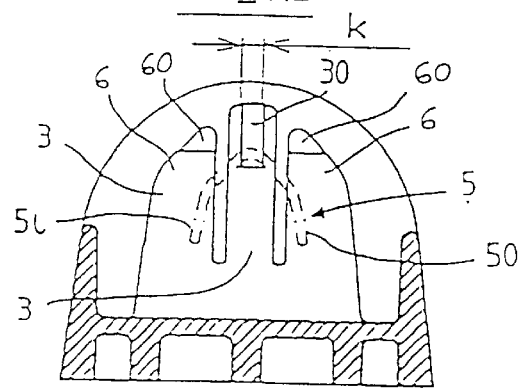
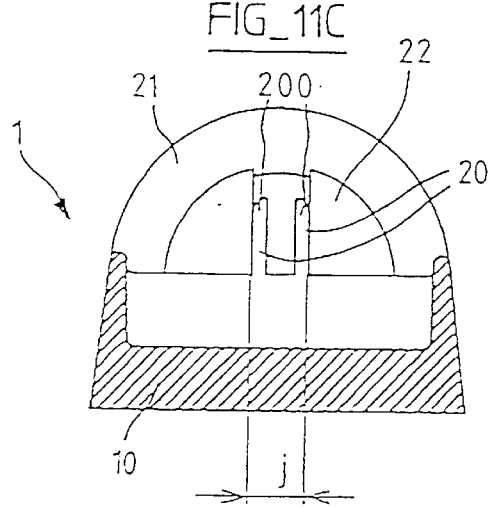
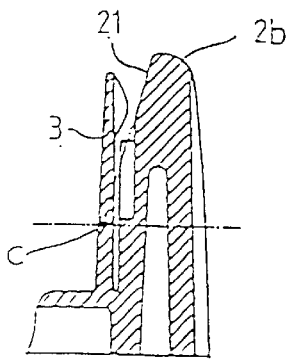
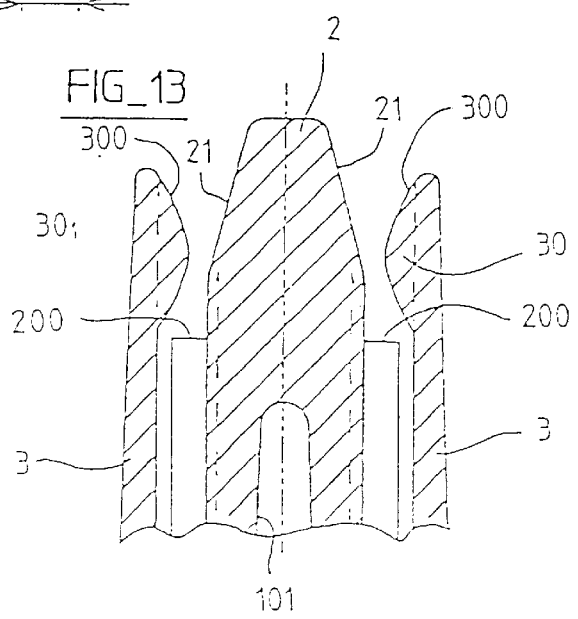

HAEMOSTATIC CLIP HOLDER

The present invention relates to a hemostatic clip holder.

A hemostatic clip is a small clamp, that is generally made of metal, that is approximately U-shaped, and that is designed to be placed and closed on a blood vessel during a surgical operation, in order to close off said vessel.

Clips are supplied to users on a support, commonly referred to as a cartridge or a strip, carrying a certain number of clips placed side by side, for example a dozen clips.

During an operation, the surgeon takes clips one by one as they are needed, using special forceps which also serve, once the clip has been taken, to transfer it onto the blood vessel, and to compress it to pinch off and close the vessel.

Clip supports generally have a certain number of housings extending transversely relative to the longitudinal direction of the strip, with the clips being engaged therein in the upside-down position (upside-down U-shape).

Devices of that kind are described, for example, in the documents U.S. Pat. No. 3,326,216 and U.S. Pat. No. 4,696,396.

In those known devices, the clips are retained by friction with the limbs of the U-shapes being prestressed in the closure direction so as to clamp against the strip wall with a certain amount of friction.

This holding force is rather unpredictable, and it is not always easy to extract a clip with the forceps since there is always a tendency for the clip support to be lifted together with the forceps being used for extraction.

It is therefore often necessary to use both hands, which is not practical for the surgeon.

Also known, from document WO-91/04925, is a clip support of the above-mentioned kind in which clips are retained by means of resilient tongues having notches which co-operate with the lateral limbs of an upside-down clip.

Although that device theoretically eliminates the above-mentioned drawback, there nevertheless remains a problem of interference between the forceps and the holding tongues, since the tongues are pressed against the limbs of the clip, and the forceps also press against those portions of the clip.

This gives rise to faulty operation. In addition, the presence of the deformable lateral tongue on each side of the clip considerably increases the width of the strip.

In the device constituting the subject matter of document U.S. Pat. No. 4,961,499, each clip is placed astride a fixed element of complementary shape between a pair of solid transverse walls serving to retain the clip. For this purpose, each of the walls has projections facing the other that are suitable for blocking the central zone of the web of the clip. The walls are flexible to some extent due to the presence of slots formed in the thickness thereof, and they can splay apart from each other temporarily by a camming effect to allow a clip to pass while it is being put into place and while it is being taken out.

In spite of that, the stiffness of the walls is relatively high, and that device does not allow clips to be extracted while applying a force that is small and constant; on the contrary, the operator encounters a hard point, and it is practically impossible to use a tool having open-ended grooves for extraction purposes. With forceps of that type, the connection between the jaws of the forceps and the clip takes place solely by friction and cannot overcome an opposing force that is high and/or suddenly applied.

The same drawbacks are to be encountered with the devices described in documents U.S. Pat. No. 4,076,120 and EP-A-0 482 861 which, like the preceding device, block the central zone of the web of the clip by means of two elements facing each other symmetrically about the plane of the clip, and capable of deforming over a stroke that is very limited.

The device of document EP-A-0 583 151, which is derived from EP-A-0 482 861, relates to a clip having a special shape that is not symmetrical. It has a small resilient tongue in the form of a hook acting laterally against the clip. That device has a configuration which gives the tongue an elastic stroke which is likewise very limited; in addition it is not adapted to support and retain clips that are U-shaped.

The present invention seeks to solve those problems by proposing a hemostatic clip support of the abovementioned kind that is designed to receive clips that are generally of an approximate U-shape, which support is of simple design, and retains all of the clips properly while being easy to use both when putting the clips into place in the factory and when the surgeon extracts them during an operation, it being possible to extract a clip while developing a force that is relatively small and substantially constant, even when using forceps having open-ended grooves.

The clip support applies to a set of clips that are approximately U-shaped, each comprising a web portion and a pair of lateral limbs, and the support consists in an elongate strip presenting means for supporting and retaining the clips individually side by side in an upside-down position, and in parallel transverse planes, said means co-operating exclusively with the web portions of a clip, leaving the lateral branches thereof free.

The support is remarkable by the fact that the means for supporting and retaining each of the clips consists firstly in a fixed portion carrying at least a bearing face against which the web portion of the clip rests, and secondly in a moving portion in the form of a thin tongue that is elastically deformable in bending, of a length that is at least equal to, and preferably greater than the height of the clip, and that includes at its top portion a blocking tab of bulging convex shape for bearing against the central zone of said web portion of the clip to retain it, these two portions having converging inlet walls for guiding the clip and for moving the blocking tab away temporarily while the clip is being put into place.

Thus, in the support of the invention, the means which support and block each clip are not symmetrically configured about the plane containing the clip. On the contrary, they are dissociated, with the (fixed) means for bearing against the clip being situated on one side, while the (moving) means for blocking it are situated on the other side.

Because the tongue is long and thin, it is very flexible (it has low stiffness) thus enabling the clip to be taken hold of and extracted "gently" by means of a set of forceps while using a force that is small and practically constant, and even when the forceps has groove ends that are open.

The flexible tongue can bend away from the fixed portion, following a part that is perpendicular to the plane of the clip.

Furthermore, according to certain additional and non-limiting characteristics of the invention:

the fixed portion possesses two bearing faces which support intermediate zones of the clip situated between its central zone and its lateral limbs;

the fixed portion possesses an end-of-stroke abutment-forming face for the clip-extraction forceps; and the various fixed and deformable portions are placed head-to-tail in pairs such that each of the fixed portions, other than the end fixed portions, serves to retain two clips in association with two deformable tabs.

This disposition makes it possible to make the device more compact.

In a possible embodiment, more particularly adapted to clips of small or medium size, the tongue-shaped moving portion is of a width that is substantially smaller than the width of a clip, and it is located between fixed elements which the lateral limbs of a clip are placed to face.

By means of this disposition, since the limbs of the forceps are necessarily positioned facing elements that are fixed, incorrectly placing the forceps does not run the risk of applying force prematurely to the tongue, thereby causing a clip to be extracted in untimely manner.

Other characteristics and advantages of the invention appear from the following description of a preferred embodiment made with reference to the accompanying drawings, in which:

FIG. 1 is a side view of the support, partially in section on a longitudinal vertical plane;

FIG. 2 is a plan view of the FIG. 1 support, partially in section on a horizontal plane;

FIGS. 3 and 4 are cross-section views, respectively on planes referenced III—III and IV—IV in FIG. 1;

FIG. 5 is a diagrammatic cross-section showing how a clip is taken by means of appropriate forceps;

FIG. 6 shows a clip; and

FIG. 7 is a diagram on a large scale showing how a clip is clamped on the support when it is engaged thereon (while it is being put into place in the factory).

FIGS. 8 to 13 show a variant of the support:

FIGS. 8, 9, and 10 are views from beneath, from the side in partial section, and from above said variant, respectively;

FIGS. 11A, 11B, and 11C are cross-section views on planes A—A, B—B (discontinuous section plane) and C—C (discontinuous section plane) respectively in FIG. 9;

FIG. 12 is a detail of FIG. 9, showing one end of the support; and

FIG. 13 is a detail view on a large scale, showing the detail in the circle identified by XIII in FIG. 9.

The hemostatic clip support shown in FIGS. 1 to 4 is a block 1 of plastics material that presents a certain amount of resilience. For example, it is made of injection molded polycarbonate. The block is generally in the form of a rectangular parallelepiped whose bottom portion 10 is solid, possessing a plane bottom face designed to be placed on a table or any other horizontal support.

The clip support is normally held via its ends between the thumb and forefinger. To make holding the strip more comfortable and more reliable, its ends advantageously present surfaces that are concave lightly ribbed, and of ergonomic shape so as to reduce any risk of the strip accidentally slipping on a surgical glove that might be wet.

The top portion of the block is organized to receive a set of hemostatic clips 5 side by side, as represented by discontinuous lines in FIGS. 1 to 4.

As shown in FIG. 6, the clip 5 is generally in the form of an upside-down U-shape having two lateral limbs 50 and a web portion 51, 52.

This web portion is generally V-shaped with its central zone being referenced 52 and its own limbs being referenced 51. The angle of the V-shape, referenced $\alpha$, may have a value of 90°, for example.

The limbs 50 also diverge, but only very slightly, at an angle $\beta$ of about 15°.

Clips of various dimensions can naturally be provided, as a function of applications.

By way of indication, a "large" clip could have a height $l_1$ of about 11 mm and a width $l_2$ of about 10 mm.

For a "small" clip, $l_1$ and $l_2$ could have values of about 3 mm to 4 mm.

The clip is made of wire, preferably titanium wire, having a section that is approximately in the form of an equilateral triangle with rounded corners, the size of the section (side of the triangle) lying in the range 0.2 mm to 1 mm, for example.

Naturally, the dimensions of the support match those of the clips which it is to contain.

By way of indication, for small clips, the support 1 may be 28 mm long, 12 mm wide, and 9 mm high, for example.

The support is adapted to receive ten clips side by side in the upside-down position (opening of the U-shape facing downwards), with the plane of each clip occupying a transverse vertical plane referenced T in FIG. 1.

Each clip 5 is held captive between a fixed portion 2 and an elastically deformable portion 3.

These two portions are portions integrally molded with the bottom portion 10.

The portions 2 and 3 are generally in the form of transverse plates, the relatively thicker plates 2 being undeformable, while the thinner plates 3 are, on the contrary, tongues that are elastically deformable in bending in the longitudinal direction (perpendicularly to the transverse planes T).

They can bend relative to their zones where they join the portion 10 of the support, since the constituent plastics material has elastic properties that are selected to make such bending possible.

According to an important characteristic of the invention, the length 1 corresponding to the flexible zones of the tongues 3 is at least equal to, and is preferably greater than, the height $l_1$ of the clips.

With reference to FIGS. 3 and 4, it will be observed that lateral longitudinal ribs 100 are present to stiffen the block 1, so that the gripping force applied by the operator does not interfere with clip extraction. In addition, the ribs provide a wall for protecting the clips.

With the exception of the end fixed portions 2a and 2b, each fixed portion 2 co-operates via each of its two opposite faces with a respective one of the deformable portions 3, the assembly having a "head to toe" configuration which can readily be seen in FIGS. 1 and 2.

The faces of the portions 2 that face a respective deformable portion 3 have two parallel vertical ribs 20 (see FIG. 3) whose chamfered top edges 200 are shaped to bear against the portions 51 of a clip.

At a level higher than the level of the bearing faces 200, each portion 2 has a facet 21 designed to bear against the flank of a clip, in the vicinity of its central zone 52.

As can be seen more particularly in FIG. 7, this facet 21 is inclined so as to come closer to the moving portion 3 with which it is associated on going downwards.

On its face facing towards the associated fixed portion 2, each deformable portion 3 has a bulging retaining tab 30.

This is shaped and positioned so as to press appropriately against the top of the zone 52 of a clip, on its flank opposite from the flank which bears against the facet 21.

As can be seen in FIG. 2, the tab 30 has a middle axial position between the two ribs 20.

Facing these portions 20, the portion 3 is hollowed out and presents two vertical grooves 31.

As can be seen in FIG. 7, the bulging tab 30 has an inclined inlet face 300 in a disposition that is substantially symmetrical (about a transverse plane) to that of the fixed facet 21. This figure shows the triangular outline with rounded corners of the section of a clip, and more particularly of the section of its central zone 52.

The triangle is substantially an equilateral triangle in shape with one of its sides being horizontal. It will be understood that when the clip is put into place on the support, which operation takes place in a factory, the portion 52 is guided between the inclined faces 21 and 30 as the clip is pushed downwards.

The fixed facet 21 acts as a ramp urging the clip axially, which in turn pushes against the resilient tab 30 (arrow F in FIG. 7).

Once the base of the section of zone 52 has gone past the bulging portion of the tab 30, the tab can deform in the direction opposite to F, over a stroke that is nevertheless limited, so as to press against the zone 52, thereby pressing it elastically both against the bearing faces 200 and against the base of the facet 21.

The resilient tab 30 thus exerts a force that acts both axially towards the fixed element 2, and downwards, due to the triangular shape of the section of the clip.

The clip is thus securely held in the support via its zone 52 and its intermediate limbs 51.

In contrast, its limbs 50 are entirely free, and accessible so as to make extraction of the clip by means of forceps very convenient.

In the diagram of FIG. 7, $P_0$ refers to the outline of the flexible portion 3 prior to a clip being put into place, $P_M$ shows the position of maximum deflection while the clip is being put into place, and $P_F$ shows the final position in which the tab 30 holds the clip against its support.

As an indication, various functional dimensions referenced in the diagram of FIG. 7 are given below:

spacing at the inlet between the facets 21 and 300: e=2 mm;

maximum push-back stroke of the moving tab: d=0.33 mm;

push-back stroke of the tab 30 when holding the clip: d'=0.15 mm;

downward stroke of the clip for pushing back the moving tab 30: h=1.35 mm; and axial translation of the clip while being pushed down: i=0.24 mm.

FIG. 5 shows a clip being taken hold of an extracted by means of forceps whose two jaws are referenced M.

Fine chain-dotted lines referenced $M_0$ show the jaws of the forceps prior to engaging the clip.

In conventional manner, these jaws have longitudinally-extending open-ended grooves R (open bottom ends), which are clamped against the outside edges of the limbs 50.

One of these grooves can be seen in the left-hand jaw which is shown in section in FIG. 5.

It will be understood from observing FIG. 5 that the jaws can be lowered freely since there is no element of the support 1 present in the zone where the jaws M take action.

The jaws pinch the clip to a certain extent while they are being lowered (thereby closing the U-shape) thus enabling them to hold it by friction.

The down stroke of the forceps is limited by abutment-forming horizontal faces 220 extending outwards from the elements 20.

The operator therefore has no need to grope. At the end of the stroke, the clip is properly placed in the forceps.

All the operator needs to do is exert vertical traction upwards in the plane T of the clip.

The clip is disengaged by a ramp effect operating in the opposite direction to that which applies while it is being put into place, as described above with reference to FIG. 7.

The portion 52 of the clip which rubs against the bulging wall of the tab 30 causes the tab to move away along arrow F, and the clip is quickly released.

It is possible to take a clip using forceps and only one hand, with the force required for extracting a clip being small and regular, being practically constant (no hard point), and insufficient for lifting the support.

Nevertheless, in conventional manner, it can be useful to engage the support in a heavy slab.

This option is shown in FIG. 4 where the outline of a slab is drawn in chain-doted lines.

To this end, the base 10 of the support advantageously has side faces that slope so as to form a dovetail suitable for being engaged in a groove (slideway) of complementary shape formed in the slab.

Another solution can consist in sticking a double-sided adhesive film to the bottom face of the support 1. When surgery is taking place, the operator can thus stick the support 1 to an appropriate support, e.g. on one of the operator's gloves.

In a possible variant of the support (not shown), the tab 30 can be moved away in the direction F by action of the forceps as it is inserted into the support. For this purpose, it suffices to provide ramps of appropriate shape on the resilient portion 3 against which the lateral zones of the jaws of the forceps can bear as they move downwards, thereby releasing the clip. This reduces the force required for extraction.

The support constituting the variant shown in FIGS. 8 to 13 is particularly adapted to clips that are of small or medium size. It is adapted to receive six clips.

In these figures, the same reference digits are used for designating elements that are identical or similar to elements of the support as described above.

It will be observed that the bottom portion of the support 1 has gaps 101 for reducing its weight, some of which gaps extend inside the fixed portions 2. It would also be observed that the support has concave ends 102 that are easy to hold in the hand.

As can be seen more particularly in FIGS. 9, 11A, and 11B, the thin and resilient tongue 3 is of small width i; it occupies only the central portion of the support. Its thickness (visible in FIG. 9) tapers upwards giving it a triangular cross-section; in this way bending stress is substantially constant up its entire height.

This height is greater than the height of a clip, as shown in FIG. 11B where a clip (in place on the support) is shown in dashed lines.

The bulging tab 30 occupies the central zone of the top portion of the tongue. Its width k is, for example, half the width i.

In FIG. 11C, i designates the width of the bearing elements 20.

This width is perceptibly greater than the above-mentioned width i.

On either side, the tongue 3 faces an upwardly extending fixed element 6. The top edges 60 of the elements 6 are slightly chamfered.

The elements 6 constitute pillars connected via their bases to the bottom portion of the element 1.

The transverse faces of the elements 6 facing the associated fixed portion 2 lie substantially in the same plane as the corresponding face of the tongue 3.

The free lateral limbs 50 of the clip consequently lie between two fixed faces, such that putting the forceps into place for extracting a clip does not run the risk of applying untimely force to the resilient tongue. Force is applied to the tongue only during the subsequent extraction, after the grooves of the forceps have been properly engaged on the limbs 50. The chamfered edges 60 facilitate guidance of the forceps.

The elements 6 (and their chamfers 60) are of a height such that the jaws of the forceps are guided even before the jaws make contact with the clip.

It will be observed that the fixed ramp 21 is frustoconical in shape, with the half-angle at its apex having a value of 75°, for example, and with its virtual apex referenced C in FIG. 12 lying in the central zone of the associated tongue.

This frustoconical portion is intersected by transverse vertical faces 22 on either side of the tongue (see FIG. 11C).

By way of indication, for a support that is designed to receive clips having a height $l_1$ of about 4 mm to 5 mm, the following dimensions are used: l=8 mm to 10 mm; i=2.5 mm to 3.5 mm; i=2 mm; and k=1 mm.

What is claimed is:

1. A hemostatic clip support for supporting a set of clips (5) that are approximately U-shaped, each comprising a web portion (51–52) and a pair of lateral limbs (50), the support (1) comprising an elongate strip having means for individually support and retaining the clips side by side in an upside-down position in parallel transverse planes (T), wherein said means co-operate exclusively with the web portions (51–52) of the clip (5), while the lateral branches (50) thereof are free, the support being characterized by the fact that said means for supporting and retaining each of the clips (5) consists firstly in a fixed portion (2) carrying at least a bearing face (200) against which the web portion (51–52) of the clip (5) rests, and secondly in a moving portion (3) in the form of a thin tongue that is elastically deformable in bending, of a length (1) that is at least equal to the height ($l_1$) of the clip, and that includes at its top portion a blocking tab (30) of bulging convex shape for bearing against the central zone (52) of said web portion of the clip to retain it, these two portions (2, 3) having converging inlet walls (21, 300) for guiding the clip (5) and for moving the blocking tab (30) away temporarily while the clip is being put into place.

2. A support according to claim 1, characterized by the fact that the fixed portion (2) possesses two bearing faces (200) which support intermediate zones (51) of the clip (5) situated between its central zone (52) and its lateral limbs (50).

3. A support according to claim 1 or 2, characterized by the fact that the fixed portion (2) possesses an end-of-stroke abutment-forming face (220) for the clip-extraction forceps.

4. A support according to claim 1 or 2, characterized by the fact that the various fixed and deformable portions (2, 3) are placed head-to-tail in pairs such that each of the fixed portions (2), other than the end fixed portions (2a, 2b), serves to retain two clips (5) in association with two deformable tabs (30).

5. A support according to claim 1 to 2, characterized by the facts that said tongue-shaped moving portion (3) is of a width (i) that is substantially smaller than the width of a clip (5), and that it is located between fixed elements (6) which the lateral limbs (50) of a clip are placed to face.

6. A support according to claim 3, characterized by the fact that the various fixed and deformable portions (2, 3) are placed head-to-tail in pairs such that each of the fixed portions (2), other than the end fixed portions (2a, 2b), serves to retain two clips (5) in association with deformable tabs (30).

7. A support according to claim 3, characterized by the facts that said tongue-shaped moving portion (3) is of a width (i) that is substantially smaller than the width of a clip (5), and that it is located between fixed elements (6) which the lateral limbs (50) of a clip are placed to face.

8. A support according to claim 4, characterized by the facts that said tongue-shaped moving portion (3) is of a width (i) that is substantially smaller than the width of a clip (5), and that it is located between fixed elements (6) which the lateral limbs (50) of a clip are placed to face.

* * * * *

UNITED STATES PATENT AND TRADEMARK OFFICE
CERTIFICATE OF CORRECTION

PATENT NO. : 6,158,583
DATED : December 12, 2000
INVENTOR(S) : Forster

Page 1 of 1

It is certified that error appears in the above-identified patent and that said Letters Patent is hereby corrected as shown below:

<u>Title page,</u>
Item [54], Title, please delete "HAEMOSTATIC CLIP HOLDER" and insert
-- A HEMOSTATIC CLIP HOLDER --.

Item [86], PCT Publication Date, please delete "Dec. 2, 1998" and insert
-- Feb. 12, 1998 --.

Signed and Sealed this

Nineteenth Day of February, 2002

Attest:

Attesting Officer

JAMES E. ROGAN
Director of the United States Patent and Trademark Office